US011761885B1

(12) United States Patent
Mansour et al.

(10) Patent No.: US 11,761,885 B1
(45) Date of Patent: Sep. 19, 2023

(54) DEVICE FOR DETERMINING FISH GENDER

(71) Applicant: KING FAISAL UNIVERSITY, Al-Ahsa (SA)

(72) Inventors: Abdallah Tageldein Mansour, Al-Ahsa (SA); Ahmed Saud Alsaqufi, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/144,157

(22) Filed: May 5, 2023

(51) Int. Cl.
*G01N 33/92* (2006.01)
*G01N 21/25* (2006.01)
*G01N 33/543* (2006.01)
*A61B 10/00* (2006.01)

(52) U.S. Cl.
CPC ..... *G01N 21/251* (2013.01); *G01N 33/54386* (2013.01); *G01N 33/92* (2013.01); *A61B 10/00* (2013.01); *G01N 2333/775* (2013.01); *G01N 2470/04* (2021.08)

(58) Field of Classification Search
CPC ....... G01N 21/251; G01N 33/92; A61B 10/00
See application file for complete search history.

(56) References Cited

U.S. PATENT DOCUMENTS

| | | |
|---|---|---|
| 2013/0244261 A1 | 9/2013 | Wetzel et al. |
| 2021/0379118 A1 | 12/2021 | Lonne et al. |

FOREIGN PATENT DOCUMENTS

CN 114705878 A * 7/2022

OTHER PUBLICATIONS

Reinhard Schubring, "Differential scanning calorimetric (DSC) measurements on the roe of rainbow trout (*Oncorhynchus mykiss*): influence of maturation and technological treatment", Nov. 26, 2003 (Year: 2003).*
David K. Gillespie, Plasma calcium as a surrogate measure for vitellogenin in fathead minnows (*Pimephales promelas*), Sep. 15, 2003 (Year: 2003).*
Na Na Kim, "Upregulation of estrogen receptor subtypes and vitellogenin mRNA in cinnamon clownfish *Amphiprion melanopus* during the sex change process: Profiles on effects of 17β-estradiol", 2010 (Year: 2010).*

(Continued)

*Primary Examiner* — Maurice C Smith
(74) *Attorney, Agent, or Firm* — Nath, Goldberg & Meyer; Richard C. Litman (57) ABSTRACT

The device for determining fish gender includes a housing having a transparent window mounted in an upper wall of the housing. A photodetector is mounted over the transparent window. An ELISA plate is provided, including at least one positive well for containing at least one sample known to test positive for vitellogenin, at least one negative well for containing at least one sample known to test negative for vitellogenin, and at least one test well for containing at least one sample to be tested. The photodetector detects colors associated with each sample, and a determination of fish gender is made based on a comparison of the color of the at least one sample to be tested against the colors of the samples known to test positive and negative for vitellogenin, where the presence of vitellogenin indicates a female fish, and the absence of vitellogenin indicates a male fish.

20 Claims, 5 Drawing Sheets

(56) References Cited

OTHER PUBLICATIONS

B. Srinivasa Reddy, Methyl farnesoate induced ovarian vitellogenin syntehsis in freshwater rice field crab *Oziothelphusa senex* senex Fabricious, 2015 (Year: 2015).*

Heppell, Scott A. et al. "Identification of gender and reproductive maturity in the absence of gonads: muscle tissue levels of sex steroids and vitellogenin in gag (*Mycteroperca microlepis*)." Canadian Journal of Fisheries and AquaticSciences 57.1 (2000): 148-159.

Singh, Harpal et al. "A handy field-portable ELISA system for rapid onsite diagnosis of infectious diseases.". Japanese journal of infectious diseases 69.5 (2016): 435-438.

Berg, Brandon et al. "Cellphone-based hand-held microplate reader for point-of-care testing of enzyme-linked immunosorbent assays." ACS nano 9.8 (2015): 7857-7866.

"VTG elisa kit :: Grouper Vitellogenin ELISA Kit"; printed on Apr. 4, 2023 from https://www.mybiosource.com/vtg-elisa-kits/vitellogenin/280553.

"Grouper Vitellogenin, Vtg ELISA Kit"; printed on Apr. 4, 2023 from https://mw.arp1.com/grouper-vitellogenin-vtg-elisa-kit-csb-e14116fh.html.

"Mini ELISA Plate Reader"; printed on Apr. 4, 2023 from hftps://www.biolegend.com/en-us/elisa-plate-reader.

* cited by examiner

DEVICE FOR DETERMINING FISH GENDER

BACKGROUND

1. FIELD

The disclosure of the present patent application relates to testing of biological samples, and particularly to a device for determining fish gender based on a colorimetric analysis of enzyme-linked immunosorbent assay (ELISA) samples.

2. DESCRIPTION OF THE RELATED ART

A number of fish species are monandric protogynous hermaphrodites; i.e., they mature only as females and can change sex after sexual maturity. Grouper, for example, are hermaphroditic. Information on gender is particularly important for the management of hermaphroditic grouper, where increased mortality through fishing can directly affect sex ratio, and therefore the reproductive capacity of the population. Gender identification can be performed through, for example, the biopsy of gametes or external genital identification. Such identification, however, is extremely difficult when trying to control sex ratios in entire populations, particularly during spawning season. Additionally, such identification techniques are typically performed in a laboratory or other controlled setting, and may prove to be practically impossible in the wild.

Vitellogenin is an egg yolk precursor found in the females of nearly all oviparous species, including fish, amphibians, reptiles, birds, most invertebrates, and monotremes. Thus, as an alternative to biopsy and external genital identification, the determination of fish gender can be performed by testing for the presence of vitellogenin. The presence of vitellogenin in a sample taken from a fish would indicate that the fish being tested is female. However, present testing methods for determination of the presence of vitellogenin require laboratory equipment and controlled testing environments, thus also being difficult to perform in the wild. Thus, a device for determining fish gender solving the aforementioned problems is desired.

SUMMARY

The device for determining fish gender is a handheld device for determining the gender of a fish based on a colorimetric analysis of prepared enzyme-linked immunosorbent assay (ELISA) samples of serum obtained from the blood of fish. The device for determining fish gender includes a housing having an upper wall, a lower wall and at least one sidewall, with an opening being formed through the at least one sidewall. A transparent window is mounted in the upper wall of the housing, and a photodetector is mounted over the transparent window. In an exemplary device, a support may be mounted on the upper wall of the housing, and the photodetector may be mounted on a lower surface of the support. An additional light source may be provided, and the light source may also be mounted on the lower surface of the support. The light source selectively illuminates the interior of the housing beneath the transparent window.

An ELISA plate is provided including at least one positive well for containing at least one sample known to test positive for vitellogenin, at least one negative well for containing at least one sample known to test negative for vitellogenin, and at least one test well for containing at least one sample to be tested. For example, the at least one positive well for containing the at least one sample known to test positive for vitellogenin may include two such positive wells for containing two samples known to test positive for vitellogenin. Similarly, the at least one negative well for containing the at least one sample known to test negative for vitellogenin may include two such negative wells for containing two samples known to test negative for vitellogenin.

The ELISA plate is moved under the photodetector and through the opening formed through the at least one sidewall, such that the photodetector can determine a color of each sample contained in the ELISA plate. For example, the ELISA plate can be inserted manually into the housing, through the opening, and be left for a sufficient time for a color change to occur (e.g., 30 minutes). A toothed wheel may be rotatably mounted within the housing for engaging and selectively pushing individual ones of the wells of the ELISA plate, such that they are pushed, one-by-one, underneath the photodetector and light source for color scanning. The ELISA plate is pushed by the toothed wheel out of the housing, through the opening, as each well is scanned. A motor or the like may also be mounted in the housing for controllably driving the toothed wheel to rotate.

A controller in communication with the photodetector determines a first color range associated with the at least one sample known to test positive for vitellogenin, a second color range associated with the at least one sample known to test positive for vitellogenin, and at least one color associated with the at least one sample to be tested. For example, if two positive samples are provided, the samples may have differing known concentrations of vitellogenin, with one concentration representing the minimum concentration considered to be in the positive range and one concentration representing a maximum concentration. Similarly, if two negative samples are provided, the samples may have differing known concentrations of vitellogenin, with one sample having zero vitellogenin and the other sample having the maximum concentration considered to be in the negative range. Thus, the differing colors of the two positive samples define the first color range and the differing colors of the two negative samples define the second color range.

The controller then determines if the at least one sample to be tested contains vitellogenin based on a comparison of the at least one color associated therewith against the first and second color ranges. For example, four samples to be tested may be provided, and the color of each of the four samples is compared against the first and second color ranges. The controller then delivers an indication to the user that the at least one sample to be tested belongs to a female fish if it is determined that the at least one sample to be tested contains vitellogenin, or delivers an indication to the user that the at least one sample to be tested belongs to a male fish if it is determined that the at least one sample to be tested does not contain vitellogenin.

An interface may be mounted on the housing, with the interface being in communication with the controller. The interface may include a visual indicator for indicating the detected gender of the fish. The interface may also include control buttons or the like for actuating and operating the device for determining fish gender.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
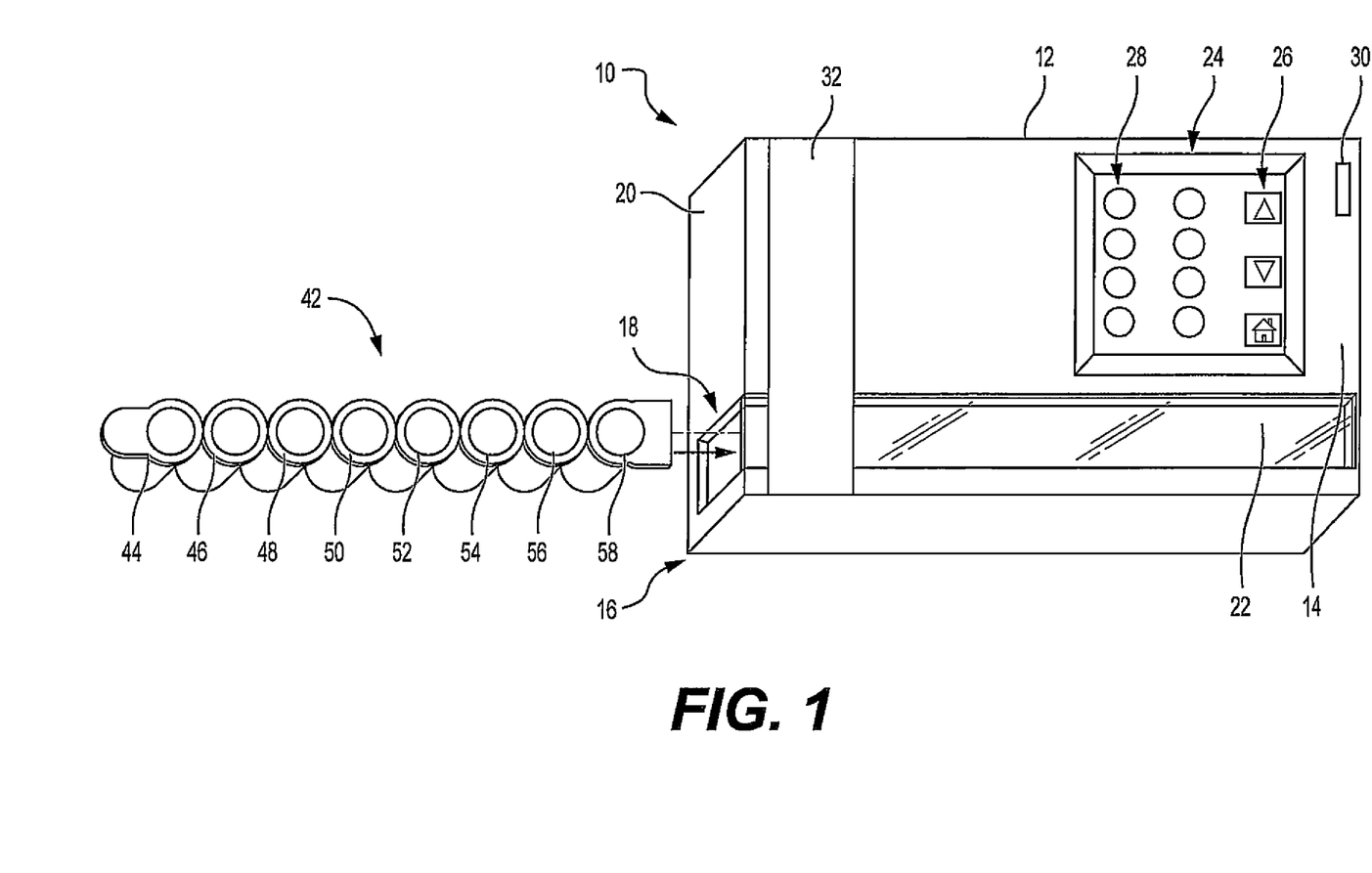
FIG. 1 is a perspective view of a device for determining fish gender, shown receiving an ELISA plate for testing.
Figure 2:
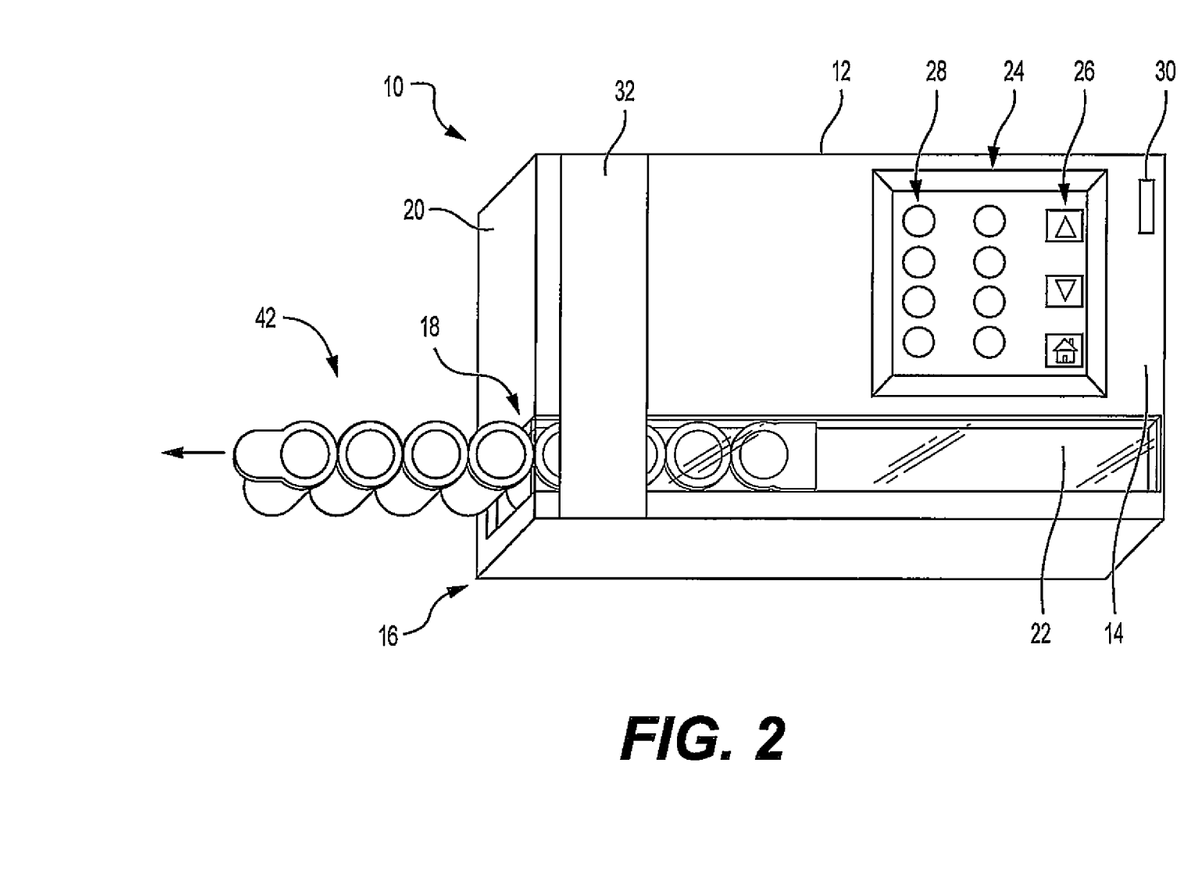
FIG. 2 is a perspective view of the device for determining fish gender, shown in the process of testing the ELISA plate.
Figure 3:
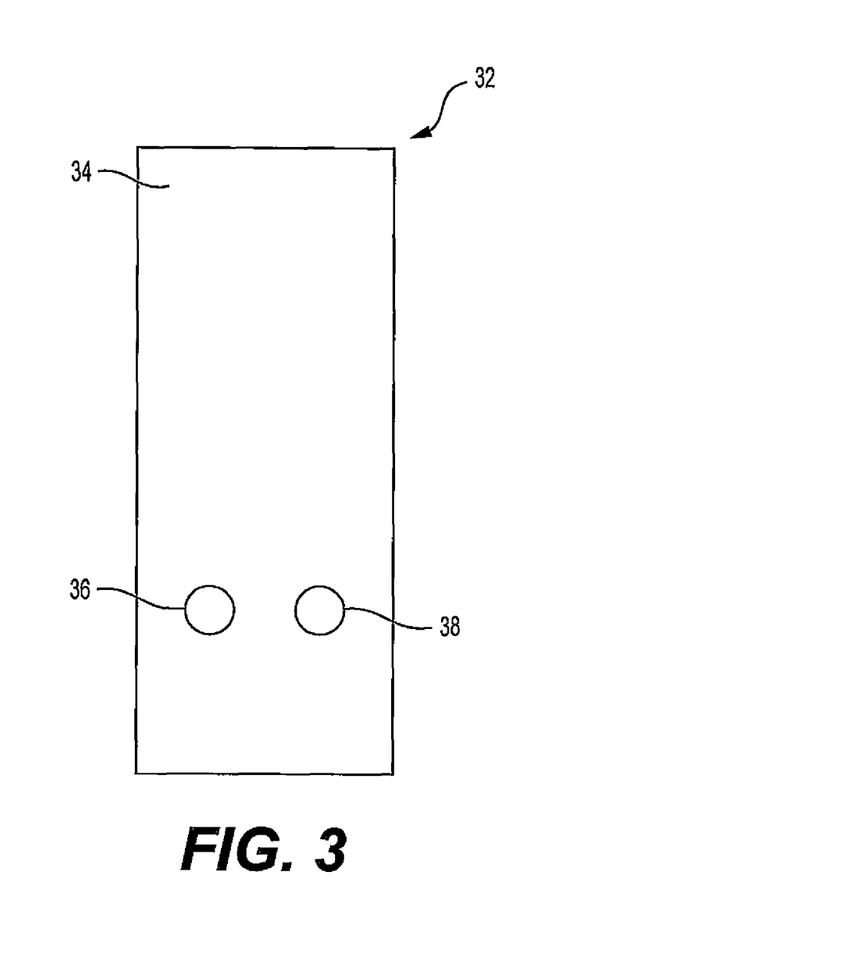
FIG. 3 is a bottom view of a support of the device for determining fish gender.
Figure 4:
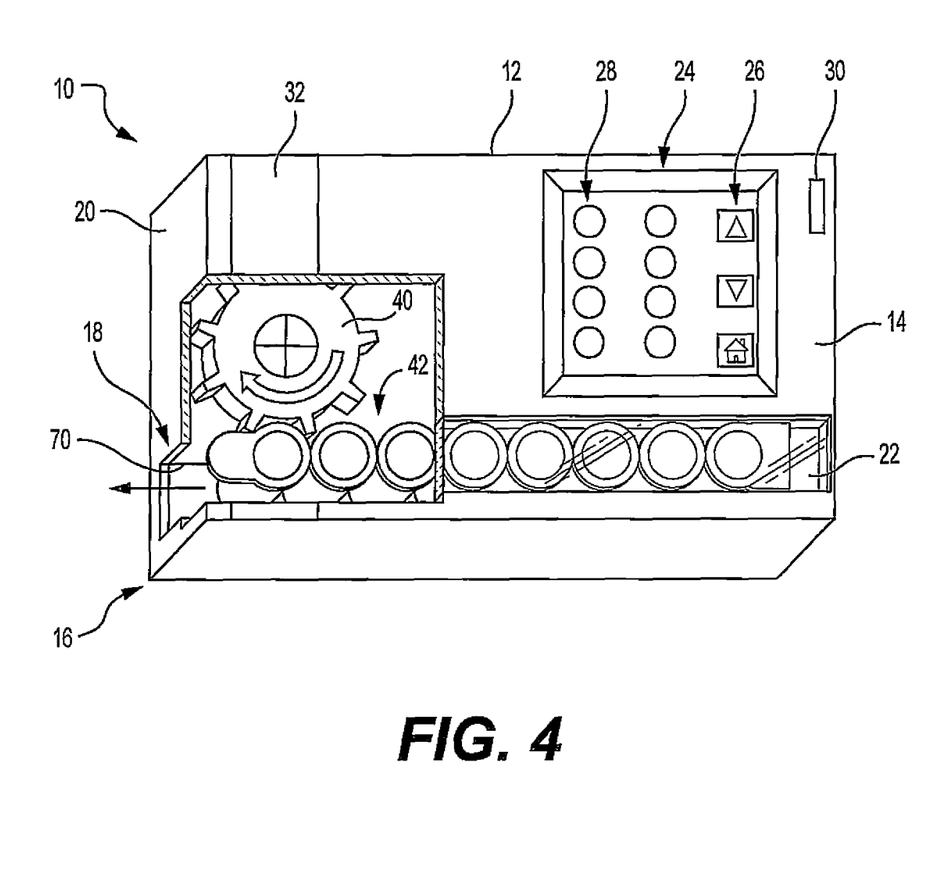
FIG. 4 is a perspective view of the device for determining fish gender, shown with a portion of the housing removed to show details thereof.

The device for determining fish gender 10 is a handheld device for determining the gender of a fish based on a colorimetric analysis of prepared enzyme-linked immunosorbent assay (ELISA) samples of serum obtained from the blood of fish. As shown in FIGS. 1-4, the device for determining fish gender 10 includes a housing 12 having an upper wall 14, a lower wall 16 and at least one sidewall 20, and an opening 18 formed in the at least one sidewall 20. It should be understood that the rectangular shape of the housing 12 in FIGS. 1, 2 and 4 is shown for exemplary purposes only, and that the housing 12 may have any suitable relative dimensions and configuration. The housing 12 is preferably configured to be handheld. For example, the housing 12 may have a rectangular shape, as shown in FIGS. 1, 2 and 4, having a width of approximately 7 cm, a length of approximately 15 cm, and a height of approximately 5 cm. Additionally, although the opening 18 is shown as being open, it should be understood that a removable or releasable door may be provided for at least temporarily covering and sealing the opening 18.

A transparent window 22 is mounted in the upper wall 14 of the housing 12 and a photodetector 36 (shown diagrammatically in FIG. 5) is mounted over the transparent window 22. In an exemplary embodiment, a support 32 may be mounted on the upper wall 14 of the housing 12, the photodetector 36 being mounted on a lower surface 34 of the support 32, as shown in FIG. 3. It should be understood that the overall configuration, relative dimensions, and positioning of both the transparent window 22 and the support 32 are shown for exemplary purposes only. It should be further understood that the transparent window 22 may be formed of any suitable optically transparent material, such as glass, clear plastic, or the like. Further, it should be understood that the photodetector 36 may be any suitable type of photodetector, photosensor, or the like capable of detecting color. As shown in FIG. 3, an additional light source 38 may be provided, and the light source 38 may also be mounted on the lower surface 34 of the support 32. The light source 38 selectively illuminates the interior of the housing 12 beneath the transparent window 22. It should be understood that the light source 38 may be any suitable type of light source, such as one or more light emitting diodes (LEDs), one or more lightbulbs, or the like.

An ELISA plate 42 is provided, including at least one positive well for containing at least one sample known to test positive for vitellogenin, at least one negative well for containing at least one sample known to test negative for vitellogenin, and at least one test well for containing at least one sample to be tested. In the exemplary embodiment of FIGS. 1, 2 and 4, the at least one positive well for containing the at least one sample known to test positive for vitellogenin includes two such positive wells 44, 46 for containing two samples known to test positive for vitellogenin. Similarly, in this exemplary embodiment, the at least one negative well for containing the at least one sample known to test negative for vitellogenin includes two such negative wells 48, 50 for containing two samples known to test negative for vitellogenin. In this exemplary embodiment, four wells 52, 54, 56, 58 are provided for containing four samples to be tested. It should be understood that any suitable type of ELISA plate may be used, such as, for example, a polystyrene microtiter plate.

In use, the ELISA plate 42 is prepared by hand-using serum extracted from fish blood. For example, a few drops of blood may be inserted into a clot activator tube to separate out the serum, and the serum may then be extracted and applied to the appropriate wells. The serum for the known positive samples is inserted into wells 44, 46, the serum for the known negative samples is inserted into wells 48, 50, and the serum for the samples to be tested is inserted into wells 52, 54, 56, 58, where any vitellogenin antigen is immobilized. A detection antibody (e.g., anti-grouper vitellogenin conjugate) covalently linked to an enzyme (e.g., horseradish peroxidase) is added, forming a complex with the vitellogenin antigen. The plate 42 is then developed by adding a substrate (e.g., p-nitrophenyl phosphate), which creates a color change to indicate the quantity of vitellogenin antigen in the sample. As in the conventional ELISA procedure, the plate 42 may be washed after immobilizing the vitellogenin (before adding the detection antibody), and again after adding the detection antibody (before adding the substrate).

Following preparation and color change, the ELISA plate 42 is moved under the photodetector 36 and through the opening 18 formed in the at least one sidewall 20, such that the photodetector 36 can determine the color of each sample contained in the ELISA plate 42. For example, the ELISA plate 42 can be inserted manually into the housing 12, through the opening 18 and be left inside the housing 12 for a sufficient time for a color change to occur (e.g., 30 minutes). As shown in FIG. 4, a toothed wheel 40 may be rotatably mounted within the housing 12 for engaging and selectively pushing individual ones of the wells 42, 46, 48, 50, 52, 54, 56, 58 of the ELISA plate 42, such that they are pushed, one-by-one, underneath the photodetector 36 and light source 38 for color scanning. The ELISA plate 42 is pushed by the toothed wheel 40 out of the housing 12, through the opening 18, as each well 42, 46, 48, 50, 52, 54, 56, 58 is scanned. A stepper motor 62 or the like may also be mounted in the housing 12 for controllably driving the toothed wheel 40 to rotate. It should be understood that any suitable type of mechanism may be used to move the ELISA plate 42 relative to the photodetector 36. For example, the toothed wheel 40 could be moved through coupling with a manual knob mounted on the housing 12. As a further alternative, the toothed wheel 40 could be replaced using any suitable type of mechanism, such as a linear actuator or the like, for moving the plate 42. In yet another alternative, the support 32 carrying the photodetector 36 could be driven to move over the transparent window 22 while the plate 42 is held still with respect to housing 12.

Figure 5:
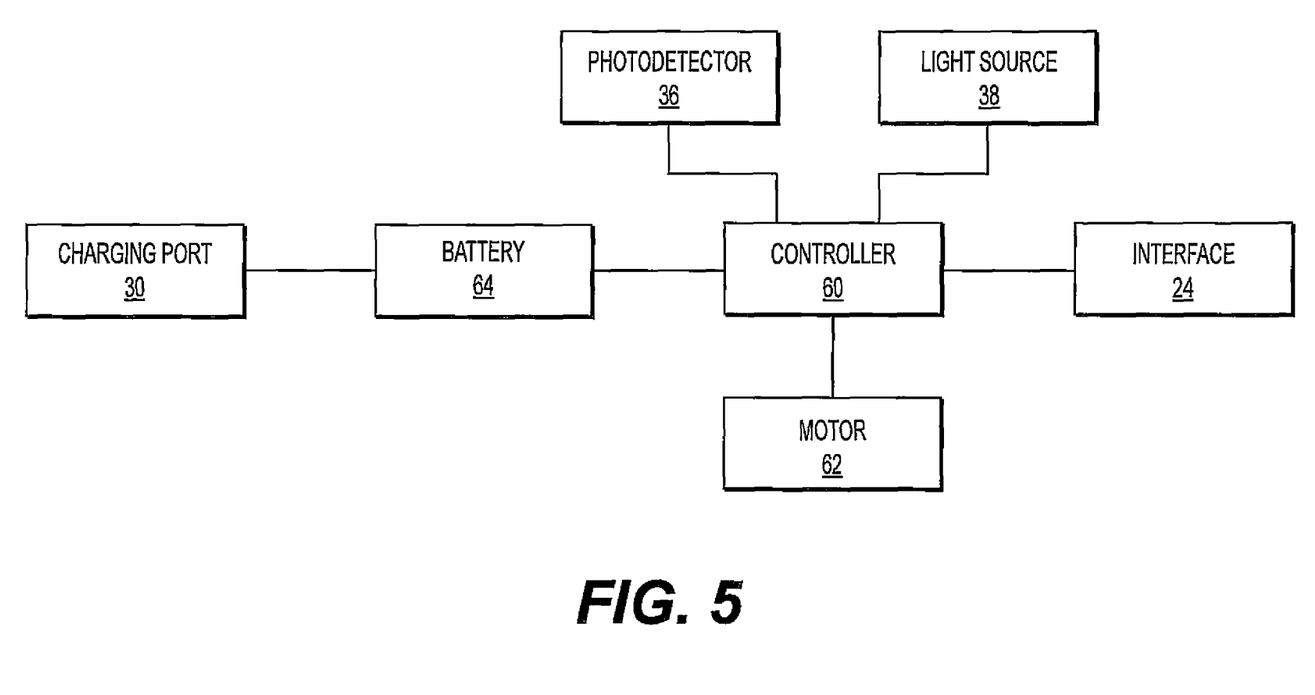
FIG. 5 is a block diagram of electrical components of the device for determining fish gender.

As shown in FIG. 5, a controller 60 in communication with the photodetector 36 determines a first color range associated with the at least one sample known to test positive for vitellogenin, a second color range associated with the at least one sample known to test positive for vitellogenin, and at least one color associated with the at least one sample to be tested. For example, if two positive samples are provided, the samples may have differing known concentrations of vitellogenin, with one concentration representing the minimum concentration considered to be in the positive range and one concentration representing a maximum concentration. Similarly, if two negative samples are provided, the samples may have differing known concentrations of vitellogenin, such as one sample having zero vitellogenin and the other sample having the maximum concentration considered to be in the negative range. Thus, the differing colors of the two positive samples define the first color range and the differing colors of the two negative samples define the second color range.

The controller 60 then determines if the at least one sample to be tested contains vitellogenin based on a comparison of the at least one color associated therewith against the first and second color ranges. For example, four samples to be tested may be provided, and the color of each of the four samples is compared against the first and second color ranges. The controller 60 then delivers an indication to the user that the at least one sample to be tested belongs to a female fish if it is determined that the at least one sample to be tested contains vitellogenin, or delivers an indication to the user that the at least one sample to be tested belongs to a male fish if it is determined that the at least one sample to be tested does not contain vitellogenin. The controller 60 may coordinate actuation of the light source 38, the photodetector 36, and the motor 62 for scanning the individual wells 42, 46, 48, 50, 52, 54, 56, 58 one at a time. The plate 42 may be mounted on a track 70, rails or the like, allowing the plate 42 to slide within the housing 12 while maintaining its relative position with respect to the transparent window 22.

An interface 24 may be mounted on the housing 12, the interface 24 being in communication with the controller 60. The interface 24 may include a visual indicator 28 for indicating the detected gender of the fish, such as colored lights or the like. The interface 24 may also include control buttons 26 or the like for actuating and operating the device for determining fish gender 10. Alternatively, the interface 24 may be a touchscreen or the like, providing both visual indication and user input.

The motor 62, the interface 24, the photodetector 36, the light source 38, and the controller 60 may be powered by an on-board rechargeable battery 64 or the like. A charging port 30, such as a universal serial bus (USB) port or the like, may be provided on the housing 12 for charging the battery 64. It should be understood that the controller 60 may be any suitable type of controller, such as a processor, programmable logic controller, computer or the like, and may be in communication with, or include, any suitable type of computer readable memory.

It is to be understood that the device for determining fish gender is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A device for determining fish gender, comprising:
    a housing having an upper wall, a lower wall and at least one sidewall, the at least one sidewall having an opening into the housing defined therein;
    a transparent window mounted in the upper wall of the housing;
    a photodetector mounted over the transparent window;
    an ELISA plate having at least one positive well for containing at least one sample known to test positive for vitellogenin, at least one negative well for containing at least one sample known to test negative for vitellogenin, and at least one test well for containing at least one sample to be tested, the ELISA plate being movable under the photodetector and through the opening formed in the at least one sidewall; and
    a controller in communication with the photodetector, the controller being configured for:
        determining a first color range associated with the at least one sample known to test positive for vitellogenin;
        determining a second color range associated with the at least one sample known to test positive for vitellogenin;
        determining at least one color associated with the at least one sample to be tested;
        determining if the at least one sample to be tested contains vitellogenin based on a comparison of the at least one color associated therewith against the first and second color ranges; and
        indicating the at least one sample to be tested belongs to a female fish when it is determined that the at least one sample to be tested contains vitellogenin, and indicating the at least one sample to be tested belongs to a male fish when it is determined that the at least one sample to be tested does not contain vitellogenin.

2. The device for determining fish gender as recited in claim 1, further comprising a support mounted on the upper wall of the housing, the photodetector being mounted on the support.

3. The device for determining fish gender as recited in claim 2, further comprising a light source mounted over the transparent window.

4. The device for determining fish gender as recited in claim 3, wherein the light source is mounted on the support.

5. The device for determining fish gender as recited in claim 1, wherein the at least one positive well for containing the at least one sample known to test positive for vitellogenin comprises two positive wells for containing two samples known to test positive for vitellogenin.

6. The device for determining fish gender as recited in claim 5, wherein the at least one negative well for containing the at least one sample known to test negative for vitellogenin comprises two negative wells for containing two samples known to test negative for vitellogenin.

7. The device for determining fish gender as recited in claim 6, wherein the two samples known to test positive for vitellogenin respectively contain different concentrations of vitellogenin.

8. The device for determining fish gender as recited in claim 7, wherein the two samples known to test negative for vitellogenin respectively contain different concentrations of vitellogenin.

9. The device for determining fish gender as recited in claim 8, wherein the at least one test well for containing the at least one sample to be tested comprises four test wells for containing four samples to be tested.

10. The device for determining fish gender as recited in claim 1, further comprising a toothed wheel engaging and selectively pushing individual ones of the wells of the ELISA plate to move the ELISA plate through the opening in the at least one sidewall under the transparent window.

11. The device for determining fish gender as recited in claim 10, further comprising a motor selectively driving the toothed wheel.

12. The device for determining fish gender as recited in claim 1, further comprising an interface mounted on the housing, the interface being in communication with the controller.

13. The device for determining fish gender as recited in claim 12, wherein the interface comprises a visual indicator for indicating a detected gender of the fish.

14. A device for determining fish gender, comprising:
a housing having an upper wall, a lower wall and at least one sidewall, the at least one sidewall having an opening into the housing defined therein;
a transparent window mounted in the upper wall of the housing;
a photodetector mounted over the transparent window;
a light source mounted over the transparent window;
an ELISA plate having at least one positive well for containing at least one sample known to test positive for vitellogenin, at least one negative well for containing at least one sample known to test negative for vitellogenin, and at least one test well for containing at least one sample to be tested, the ELISA plate being movable under the photodetector and through the opening defined in the at least one sidewall; and
a controller in communication with the photodetector and the light source, the controller being configured for:
determining a first color range associated with the at least one sample known to test positive for vitellogenin;
determining a second color range associated with the at least one sample known to test positive for vitellogenin;
determining at least one color associated with the at least one sample to be tested;
determining if the at least one sample to be tested contains vitellogenin based on a comparison of the at least one color associated therewith against the first and second color ranges; and
indicating the at least one sample to be tested belongs to a female fish when it is determined that the at least one sample to be tested contains vitellogenin, and indicating the at least one sample to be tested belongs to a male fish when it is determined that the at least one sample to be tested does not contain vitellogenin.

15. The device for determining fish gender as recited in claim 14, further comprising a support mounted on the upper wall of the housing, the photodetector and the light source being mounted on the support.

16. The device for determining fish gender as recited in claim 14, wherein the at least one positive well for containing the at least one sample known to test positive for vitellogenin comprises two positive wells for containing two samples known to test positive for vitellogenin.

17. The device for determining fish gender as recited in claim 16, wherein the at least one negative well for containing the at least one sample known to test negative for vitellogenin comprises two negative wells for containing two samples known to test negative for vitellogenin.

18. The device for determining fish gender as recited in claim 17, wherein the two samples known to test positive for vitellogenin respectively contain different concentrations of vitellogenin.

19. The device for determining fish gender as recited in claim 18, wherein the two samples known to test negative for vitellogenin respectively contain different concentrations of vitellogenin.

20. The device for determining fish gender as recited in claim 14, further comprising a toothed wheel engaging and selectively pushing individual ones of the wells of the ELISA plate; and a motor selectively driving the toothed wheel.

* * * * *